(12) United States Patent
Köll

(10) Patent No.: US 11,505,775 B2
(45) Date of Patent: Nov. 22, 2022

(54) STIRRING DEVICE WITH IMPROVED STIRRING ELEMENT CONFIGURATION

(71) Applicant: Thöni Industriebetriebe GmbH, Telfs (AT)

(72) Inventor: Thomas Köll, Telfs (AT)

(73) Assignee: Thöni Industriebetriebe GmbH, Telfs (AT)

( * ) Notice: Subject to any disclaimer, the term of this patent is extended or adjusted under 35 U.S.C. 154(b) by 730 days.

(21) Appl. No.: 16/337,789

(22) PCT Filed: Oct. 11, 2016

(86) PCT No.: PCT/EP2016/074365
§ 371 (c)(1),
(2) Date: Mar. 28, 2019

(87) PCT Pub. No.: WO2018/068836
PCT Pub. Date: Apr. 19, 2018

(65) Prior Publication Data
US 2019/0256814 A1    Aug. 22, 2019

(51) Int. Cl.
*B01F 27/00* (2022.01)
*C12M 1/06* (2006.01)
(Continued)

(52) U.S. Cl.
CPC ........... *C12M 27/06* (2013.01); *B01F 27/071* (2022.01); *B01F 27/0726* (2022.01);
(Continued)

(58) Field of Classification Search
CPC .... C12M 27/06; C12M 27/08; B01F 2101/44; B01F 2215/0427; B01F 15/0427
See application file for complete search history.

(56) References Cited

U.S. PATENT DOCUMENTS

2006/0047092 A1 *   3/2006   Marx ................. B01J 19/18
                                                                                526/64
2009/0111164 A1 *   4/2009   Schall ................ C12M 45/02
                                                                                435/263
(Continued)

FOREIGN PATENT DOCUMENTS

CH              686 085          12/1995
CN         101360816 A            2/2009
(Continued)

OTHER PUBLICATIONS

Wang, Yiding; Office Action in Application No. 201680089950.3; pp. 1-8; Dec. 29, 2020; China National ntellectual Property Administration; No. 6, Xituchneng Lu, Jimenqiao Haidian District, Beijing City, 100088, China.
(Continued)

*Primary Examiner* — Anshu Bhatia
(74) *Attorney, Agent, or Firm* — Robert A. Blaha; Smith Tempel Blaha LLC

(57) ABSTRACT

A stirring device of a plug-flow fermentation device includes a shaft rotatable about an axis of rotation which defines an axial direction. The stirring device further includes a boundary stirring element that defines the axial extent of a stirring volume covered by the stirring device. A nearest neighbor of the boundary stirring element in the axial direction has an axial maximum width which is smaller than an axial maximum width of the boundary stirring element and which is larger than an axial maximum width of a next-nearest neighbor of the boundary stirring element.

14 Claims, 2 Drawing Sheets

(51) Int. Cl.
    *B01F 27/70* (2022.01)
    *B01F 27/07* (2022.01)
    *B01F 27/112* (2022.01)
    *B01F 27/191* (2022.01)
    *B01F 27/072* (2022.01)
    *B01F 101/44* (2022.01)

(52) U.S. Cl.
    CPC .......... *B01F 27/112* (2022.01); *B01F 27/191* (2022.01); *B01F 27/70* (2022.01); *B01F 2101/44* (2022.01); *B01F 2215/0422* (2013.01); *B01F 2215/0427* (2013.01)

(56) References Cited

U.S. PATENT DOCUMENTS

| | | | | |
|---|---|---|---|---|
| 2010/0062482 | A1* | 3/2010 | Buchner | C12M 21/04 435/41 |
| 2012/0252107 | A1* | 10/2012 | Self | C12M 27/06 435/267 |

FOREIGN PATENT DOCUMENTS

| | | | |
|---|---|---|---|
| CN | 101765754 | A | 6/2010 |
| CN | 104162377 | A | 11/2014 |
| CN | 204685090 | U | 4/2015 |
| CN | 105451869 | A | 3/2016 |
| CN | 205288167 | U | 6/2016 |
| EP | 1 841 853 | | 4/2008 |
| EP | 2 034 007 | | 3/2009 |
| EP | 1 848 675 | | 8/2011 |
| EP | 2 561 925 | | 2/2013 |
| EP | 2 562 241 | | 2/2013 |
| EP | 2 837 420 | | 2/2015 |
| EP | 2 837 421 | | 2/2015 |
| EP | 2837421 | A1 | 2/2015 |
| EP | 2 948 537 | | 12/2015 |
| GB | 1 400 257 | | 7/1975 |
| JP | S60150821 | | 8/1985 |
| JP | S60150821 | A | 8/1985 |
| JP | H06352 | A | 1/1994 |
| WO | WO2012080348 | | 10/2013 |
| WO | WO2014198666 | | 12/2014 |
| WO | WO2015022305 | | 2/2015 |
| WO | WO2015198667 | A1 | 12/2015 |

OTHER PUBLICATIONS

First Notification of Office Action in Application No. 201680089950.3 (Translated); pp. 1-3; Dec. 29, 2020; China National Intellectual Property Administration.

Office Action in Application No. 201680089950.3 (Translated); pp. 1-5; Dec. 29, 2020; China National Intellectual Property Administration.

* cited by examiner

US 11,505,775 B2

STIRRING DEVICE WITH IMPROVED STIRRING ELEMENT CONFIGURATION

CROSS-REFERENCE TO RELATED APPLICATIONS

This application is a National Phase patent application and claims priority to and the benefit of International Patent Application PCT/EP2016/074365, filed on Oct. 11, 2016, the entire contents of which are incorporated herein by reference.

TECHNICAL FIELD

The present invention relates to the field of stirring devices of plug-flow fermentation devices.

TECHNOLOGICAL BACKGROUND

EP 2837421 A1 relates to a stirring device comprising a mounting structure for a stirring element and a method of mounting a stirring element. According to an embodiment, the stirring device comprises a plurality of stirring elements attached to a shaft, the plurality of stirring elements being configured differently in different axial positions of the shaft. At least one stirring element in an output region of the biogas fermenter may have larger axial and/or radial extent compared to the other stirring elements of the plurality of stirring elements.

SUMMARY

A stirring device in a plug-flow fermenter of a plug-flow fermentation device is a crucial element in the reliable and efficient operation of the plug-flow fermentation device. The stirring device may serve to homogenize and mix the content of the plug-flow fermenter. Further, the stirring device may assist exiting of the biogas from the fermentation material by agitation of the fermentation material in the plug-flow fermenter. It may be advantageous to have a plug-flow fermenter which is insensitive to heavy particulate matter in the fermentation material. Further, it may be advantageous if a transport of heavy particulate matter through the plug-flow fermenter is supported by the stirring device. Further, the faster the fermentation material is homogenized in an input region of the plug-flow fermenter (i.e. in a region where fermentation material is introduced into the plug-flow fermenter) the larger is the biologically usable fermentation volume. In the input region of the plug-flow fermenter fresh fermentation material (which is introduced into the plug-flow fermenter) has to mixed with inoculation material and fermentation material which is already present in the plug-flow fermenter. Further, the better the fermentation material is homogenized in a discharge region of the plug-flow fermenter (i.e. in a region where the fermentation material is discharged from the plug-flow fermenter) the easier is the discharging of the fermentation material in particular if the fermentation material contains heavy particulate matter.

In view of the above-described situation, there still exists a need for an improved technique that enables to provide a stirring device of a plug-flow fermentation device with improved characteristics.

This need may be met by the subject matter according to the independent claims. Advantageous embodiments of the herein disclosed subject matter are described by the dependent claims.

According to an embodiment of a first aspect of the herein disclosed subject matter there is provided a stirring device of a plug-flow fermentation device, the stirring device comprising: a shaft rotatable about an axis of rotation, the axis of rotation being parallel to an axial direction; a plurality of stirring elements including a first stirring element, a second stirring element and a third stirring element; wherein the first stirring element is a boundary stirring element defining an axial extent of a stirring volume covered by the stirring device; the second stirring element is a nearest neighbor of the first stirring element in the axial direction; the third stirring element is a next-nearest neighbor of the first stirring element in the axial direction; and in the axial direction the second stirring element has a maximum width which is smaller than a maximum width of the first stirring element and which is larger than a maximum width of the third stirring element.

According to an embodiment of a second aspect of the herein disclosed subject matter there is provided a plug-flow fermentation device for receiving a fermentation material and for fermentation of the fermentation material, the plug-flow fermentation device comprising: a plug-flow fermenter; and a stirring device according to the first aspect or an embodiment thereof, located in the plug-flow fermenter.

According to an embodiment of a third aspect of the herein disclosed subject matter there is provided a method of operating a plug-flow fermentation device comprising a plug-flow fermenter, the method comprising: stirring in the plug-flow fermenter a fermentation material which contains heavy particulate matter so as to homogenize the fermentation material at an end region of the plug-flow fermenter; wherein in particular homogenizing the fermentation material includes dispersing the particulate matter within the fermentation material.

Overview of Embodiments

In the following, exemplary embodiments of the herein disclosed subject matter are described, any number and any combination of which may be realized in an implementation of aspects of the herein disclosed subject matter. Generally herein, dimensions and distances refer to dimension and distances in axial direction (axial dimensions and distances), unless explicitly indicated to the contrary.

According to embodiments of the first aspect, the stirring device is adapted for providing the functionality or features of one or more of the herein disclosed embodiments and/or for providing the functionality or features as required by one or more of the herein disclosed embodiments, in particular of the embodiments of the second and third aspect disclosed herein.

According to embodiments of the second aspect, the plug-flow fermentation device is adapted for providing the functionality or features of one or more of the herein disclosed embodiments and/or for providing the functionality or features as required by one or more of the herein disclosed embodiments, in particular of the embodiments of the first and third aspect disclosed herein.

According to embodiments of the third aspect, the method is adapted for providing the functionality or features of one or more of the herein disclosed embodiments and/or for providing the functionality or features as required by one or more of the herein disclosed embodiments, in particular of the embodiments of the first and second aspect disclosed herein.

According to an embodiment, instead of being referred to as a boundary stirring element defining an axial extent of a stirring volume covered by the stirring device the first stirring element may also be referred to as outermost stirring element of the stirring device in the axial direction.

According to an embodiment, the stirring device further comprises a common mounting structure being associated with two axially neighboring stirring elements of the plurality of stirring elements; wherein the two axially neighboring stirring elements are both mounted to the shaft via the common mounting structure. For example, according to an embodiment that the common mounting structure may comprise two or more pieces which act together in the mounting of the two axially neighboring stirring elements to the shaft. Further, according to an embodiment one of the two or more pieces of the common mounting structure is shared by the two axially neighboring stirring elements.

A rotation of the shaft about the axis of rotation defines a circumferential direction. According to an embodiment, in the circumferential direction the third stirring element is located in an angular range between the first stirring element and the second stirring element. According to an embodiment, the first stirring element and the second stirring element divide a full circle into two segments, a larger segment and a smaller segment (i.e. the first stirring element and the second stirring element are not located diametrically opposite to each other which would result in two equal segments of 180 degrees), wherein the smaller segment is smaller than the larger segment. According to an embodiment, the angular range corresponds to the larger segment (and hence the third stirring element is located within the larger segment defined by the first stirring element and the second stirring element. According to another embodiment, the angular range is the smaller segment.

According to an embodiment, the second stirring element is located opposite the first stirring element, in an angular range between 140 degrees and 220 degrees with respect to the first stirring element. According to a further embodiment, the second stirring element is located in an angular range between 160 degrees and 200 degrees with respect to the first stirring element. According to a further embodiment, the second stirring element is located in an angular range between 170 degrees and 190 degrees with respect to the first stirring element.

According to a further embodiment the plurality of stirring elements are arranged in at least two subsets on the shaft, the at least two subsets including a first subset and a second subset, wherein the stirring elements of each subset are positioned within an angular range of ±15 degrees. According to a further embodiment, the stirring elements of each subset are positioned within an angular range of ±10 degrees, or, in other embodiments, of ±5 degrees, ±2 degrees or ±1 degree.

According to an embodiment, the first stirring element belongs to the first subset, and in the first subset there are fewer stirring elements than in the second subset. In another embodiment, the number of stirring elements in each subset is equal. For example, according to an embodiment the number of stirring elements E of the entire stirring device is N times the number F of subsets (E=N×F).

According to an embodiment, the stirring device further comprises (e.g. in an axial middle region of the shaft) two further, axially neighboring stirring elements defining in the axial direction a first minimum distance therebetween; the first stirring element and the second stirring element defining in the axial direction a second minimum distance therebetween; and wherein the first minimum distance is larger than the second minimum distance. In other words, according to an embodiment the minimum distance in axial direction between neighboring stirring elements in the end region (i.e. in the input region and/or in the discharge region) of the stirring device is smaller than in another region (e.g. the middle region) of the stirring device. The reduced minimum distance in the axial direction in the end region of the stirring device improves homogenization of the stirring material in the plug-flow fermenter.

According to a further embodiment, in the axial direction towards the boundary stirring element a distance between positions of neighboring stirring elements is reduced compared to a distance between positions of neighboring stirring elements in a middle region of the stirring device. Hence, in other words in the middle region of the stirring device the distance between positions of neighboring stirring elements is larger than in the end region of the stirring device.

According to a further embodiment, each of the stirring elements comprises a rod portion having a first width in the axial direction and a head portion which has a second width in the axial direction; and wherein in the axial direction towards the boundary stirring element the second width of the stirring elements increases. For example, according to an embodiment the second width of the third stirring element is smaller than the second width of the second stirring element and the second width of the second stirring element is smaller than the second width of the first stirring element. According to a further embodiment, the second width of the stirring elements in the middle region of the stirring device is the same (e.g. is the same within an accuracy of ±10% or within an accuracy of ±5% or within an accuracy of ±1%). According to an embodiment, the term "within an accuracy of x %" has the following meaning: If the second width of the stirring elements in the middle region is the same within an accuracy of x % (e.g. 10%) the second width of each of these stirring elements differs by x % or less from an arithmetic mean value calculated from the second widths of these stirring elements.

According to a further embodiment, the stirring device further comprises a first distance between the rod portion of the third stirring element and the rod portion of the second stirring element; and a second distance between the rod portion of the second stirring element and the rod portion of the first stirring element; wherein the first distance is different from the second distance. For example, according to an embodiment the first distance is smaller than the second distance. The first distance being smaller than the second distance may in particular be advantageous if the second width of the second stirring element is smaller than the second width of the first stirring element.

According to an embodiment, the plug-flow fermenter is configured for introduction of fermentation material the particulate matter of which has in at least two dimensions a size which is smaller than or equal to a predetermined maximum size.

According to a further embodiment, the stirring device is designed (configured) for fermentation material the particulate matter of which has in at least two dimensions a size which is smaller than or equal to a predetermined maximum size M. Further, in the axial direction a minimum distance $d_{min}$ between the first stirring element and the second stirring element is less than R times the maximum size M ($d_{min} < R \times M$), wherein R is a number in an interval $1 \leq R \leq 5$, in particular wherein R=3. According to a further embodiment, R is a number in an interval $2 \leq R \leq 4$. According to an embodiment, the predetermined maximum size is a mesh size of a sieve in an input path of the fermentation material into the plug-flow fermenter.

According to a further embodiment the stirring device is designed to be located in the plug-flow fermenter such that the first stirring element is located in a discharge region of the plug-flow fermenter. According to another embodiment, the first stirring element is located in an input region of the plug-flow fermenter.

According to an embodiment, the plug-flow fermenter of the plug-flow fermentation device (biogas plant) further comprises a fermenter wall defining a bottom of a cavity for receiving the fermentation material; the plug-flow fermenter being configured for introduction of fermentation material the particulate matter of which has in at least two dimensions a size which is smaller than or equal to a predetermined maximum size M; and wherein (in a radial direction defined by the shaft, perpendicular to the axial direction) a minimum distance rmin between the first stirring element and the fermenter wall is larger than S times the maximum size M (rmin>S×M), wherein S is a number in an interval 1≤S≤5, in particular wherein S=3. According to a further embodiment, S is a number in an interval 2≤S≤4. As mentioned above, the predetermined maximum size may be a mesh size of a sieve in an input path for inputting the fermentation material into the plug-flow fermenter.

According to a further embodiment, the plug-flow fermenter comprises a plurality of fermenter parts positioned subsequently in the axial direction, the plurality of fermenter parts comprising a first fermenter part having a first axial extent in the axial direction; the plurality of stirring elements comprising a sequence of stirring elements, the sequence of stirring element being defined in axial direction by two outermost stirring elements of the sequence, the sequence of stirring elements having a second axial extent between the axial positions of the outermost stirring elements; wherein the second axial extent differs from the first axial extent by less than 5% (or, in another embodiment, by less than 2% or even 1%) of the first axial extent.

Embodiments of the herein disclosed subject matter may be implemented in order to assist homogenizing fermentation material in the plug-flow fermenter at a discharge region, thereby conditioning the fermentation material at the discharge region within the plug-flow fermenter into a pumpable and/or suckable state. By dispersing the heavy particulate matter of the fermentation material sediments of heavy particulate matter are avoided and also the heavy particulate matter is (together with the remaining fermentation material) conditioned into a pumpable and/or suckable state. Proper homogenization (and in particular proper dispersion of heavy particulate matter) has the advantage that a discharge pump operates reliably, both at the inlet side and the outlet side of the pump. In particular, proper homogenization allows a discontinuous operation of the discharge pump wherein, within a certain time interval, e.g. within 1 to 10 hours, sediments occur at the inlet side and/or the outlet side of the discharge pump, only to such an extent that further operation of the discharge pump is possible. According to an embodiment, dispersing the heavy particulate matter includes spatial dispersing and/or temporal dispersing. According to a further embodiment, spatial dispersing includes (or is) dispersing in a plane perpendicular to the axial direction. Such a dispersion may result be effected by the rotation of the stirring device about its axis of rotation. According to a further embodiment, the temporal dispersion includes (or is) dispersion in arrival time at a discharge outlet of the plug-flow fermenter. In such a case, by temporal dispersion a discontinuous arrival of heavy particulate matter at a discharge outlet of the plug-flow fermenter is avoided or at least reduced. Further, by temporal dispersion an accumulation of heavy particulate matter (e.g. a heap on the bottom of the plug-flow fermenter) is avoided or at least reduced. In this way, an obstruction of the discharge outlet by an accumulation of the heavy particulate matter is avoided or at least the likelihood of such an obstruction is reduced. In the plug-flow fermenter, the fermentation material is moved plug-like in the axial direction (i.e. mixing of the fermenter content is performed by the stirring device essentially in a volume defined by the swiveling range of the respective stirring element perpendicular to the axial direction). Hence, in the plug-flow fermenter the temporal dispersion in arrival time at a discharge outlet corresponds (at an instant in time) to a spatial dispersion along the axial direction wherein the temporal dispersion refers to the time axis of the movement of the plug of fermentation material through the plug-flow fermenter in the axial direction. Hence, the two terms (temporal dispersion in arrival time at a discharge outlet and spatial dispersion along the axial direction) can be used interchangeably.

According to an embodiment, the dispersion of the heavy particulate matter is effected to at least 30 weight %, i.e. 30 weight % of the heavy particulate matter is equally distributed in the end region. According to other embodiments, dispersion of the heavy particulate matter is effected to at least 40 weight %, (or in other embodiments, 50 weight %, 60 weight %, 70 weight %, or even 80 weight %).

According to an embodiment, the heavy particulate matter has a density of at least 1.3 grams per cubic centimeter (1.3 $g/cm^3$). According to a further embodiment, the heavy particulate matter has a density of at least 1.5 grams per cubic centimeter or a density of at least 2.0 grams per cubic centimeter. For example, according to an embodiment, the heavy particulate matter is rock, stones, metal pieces, and/or glass pieces.

In the above there have been described and in the following there will be described exemplary embodiments of the subject matter disclosed herein with reference to a stirring device, a plug-flow fermentation device and a method of operating a plug-flow fermentation device. It has to be pointed out that of course any combination of features relating to different aspects of the herein disclosed subject matter is also possible. In particular, some features have been or will be described with reference to device type embodiments (e.g. relating to a stirring device or a plug-flow fermentation device) whereas other features have been or will be described with reference to method type embodiments (e.g. relating to a method of operating a plug-flow fermentation device). However, a person skilled in the art will gather from the above and the following description that, unless otherwise notified, in addition to any combination of features belonging to one aspect also any combination of features relating to different aspects or embodiments, for example even combinations of features of device type embodiments and features of the method type embodiments are considered to be disclosed with this application. In this regard, it should be understood that any method feature derivable from a corresponding explicitly disclosed device feature should be based on the respective function of the device feature and should not be considered as being limited to device specific elements disclosed in conjunction with the device feature. Further, it should be understood that any device feature derivable from a corresponding explicitly disclosed method feature can be realized based on the respective function described in the method with any suitable device disclosed herein or known in the art.

The aspects and embodiments defined above and further aspects and embodiments of the herein disclosed subject matter are apparent from the examples to be described hereinafter and are explained with reference to the drawings, but to which the invention is not limited. The aforementioned definitions and comments are in particular also valid for the following detailed description and vice versa.

DETAILED DESCRIPTION OF ILLUSTRATED EMBODIMENTS

Figure 1:
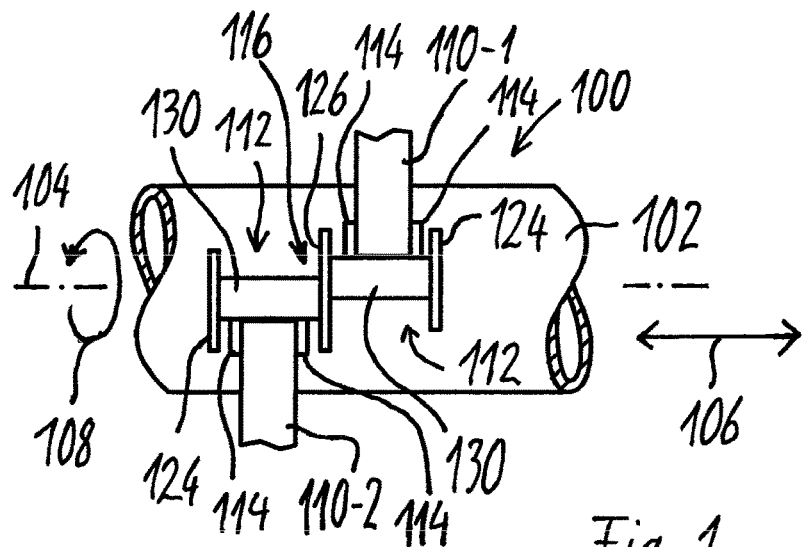
FIG. 1 shows a plan view of a part of a stirring device of a plug-flow fermentation device according to embodiments of the herein disclosed subject matter.

The illustration in the drawings is schematic. It is noted that in different figures, similar or identical elements are provided with the same reference signs. Accordingly, the description of the similar or identical features is not repeated in the description of subsequent figures in order to avoid unnecessary repetitions. Rather, it should be understood that the description of these features in the preceding figures is also valid for the subsequent figures unless explicitly noted otherwise.

FIG. 1 shows a plan view of a part of a stirring device 100 of a plug-flow fermentation device (i.e. a biogas plant of the plug-flow type) according to embodiments of the herein disclosed subject matter.

In a plug-flow fermenter the fermentation material is moved through the fermenter by introducing fresh material at a fermenter input of the plug-flow fermenter and discharging fermented material at a fermenter output of the plug-flow fermenter. According to an embodiment, the stirring device is in particular suitable for plug-flow fermenters wherein the fermentation material has a dry matter content of e.g. 15 weight % or more, e.g. of 20 weight % or more, e.g. of 25 weight % or more or 30 weight % or more.

According to an embodiment, the stirring device 100 comprises a shaft 102 which is rotatable about an axis of rotation 104. The axis of rotation 104 is parallel to an axial direction 106 of the stirring device 100 and a rotation of the shaft 102 about the axis of rotation 104 defines a circumferential direction 108. According to an embodiment, the shaft 102 is a hollow shaft defining an outer diameter and an inner diameter, the difference of which defines the wall thickness of the shaft 102.

According to a further embodiment, the stirring device 100 comprises a plurality of stirring elements of which two stirring elements, a first stirring element 110-1 and a second stirring element 110-2, are shown in part in FIG. 1. By rotating the shaft 102 about the axis of rotation 104 the stirring elements 110-1, 110-2 move in the circumferential direction 108 and thereby agitate fermentation material located in a plug-flow fermenter of a plug-flow fermentation device (not shown in FIG. 1).

According to an embodiment, the stirring elements 110-1, 110-2 are attached to the shaft 102 by at least one mounting structure 112. According to an embodiment, the mounting structure 112 comprises a first mounting part 124 and a second mounting part 126 which are spaced from each other in the axial direction 106. An intermediate part 130 is attached to the first mounting part 124 and the second mounting part 126, e.g. by welding. Each stirring element 110-1, 110-2 is attached to the intermediate part 130 of its associated mounting structure 112 by suitable mounting elements 114, e.g. bolts such as e.g. threaded bolts. According to an embodiment, two mounting structures 112 are associated with each of the stirring elements 110-1, 110-2. For example, according to an embodiment the tool associated mounting structures 112 of each stirring element are located on opposite sides of the shaft. According to an embodiment, the mounting structures may be configured as described in the European patent application number EP 2837421 A1, filed by the same applicant.

According to an embodiment, a common mounting structure 116 is associated with two axially neighboring stirring elements 110-1, 110-2. For example, according to an embodiment the common mounting structure 116 comprises the functionality of two mounting structures 112 which share a common part, e.g. the second mounting part 126, as shown in FIG. 1. The two axially neighboring stirring elements 110-1, 110-2 are both mounted to the shaft 102 via the common mounting structure 116.

Figure 2:
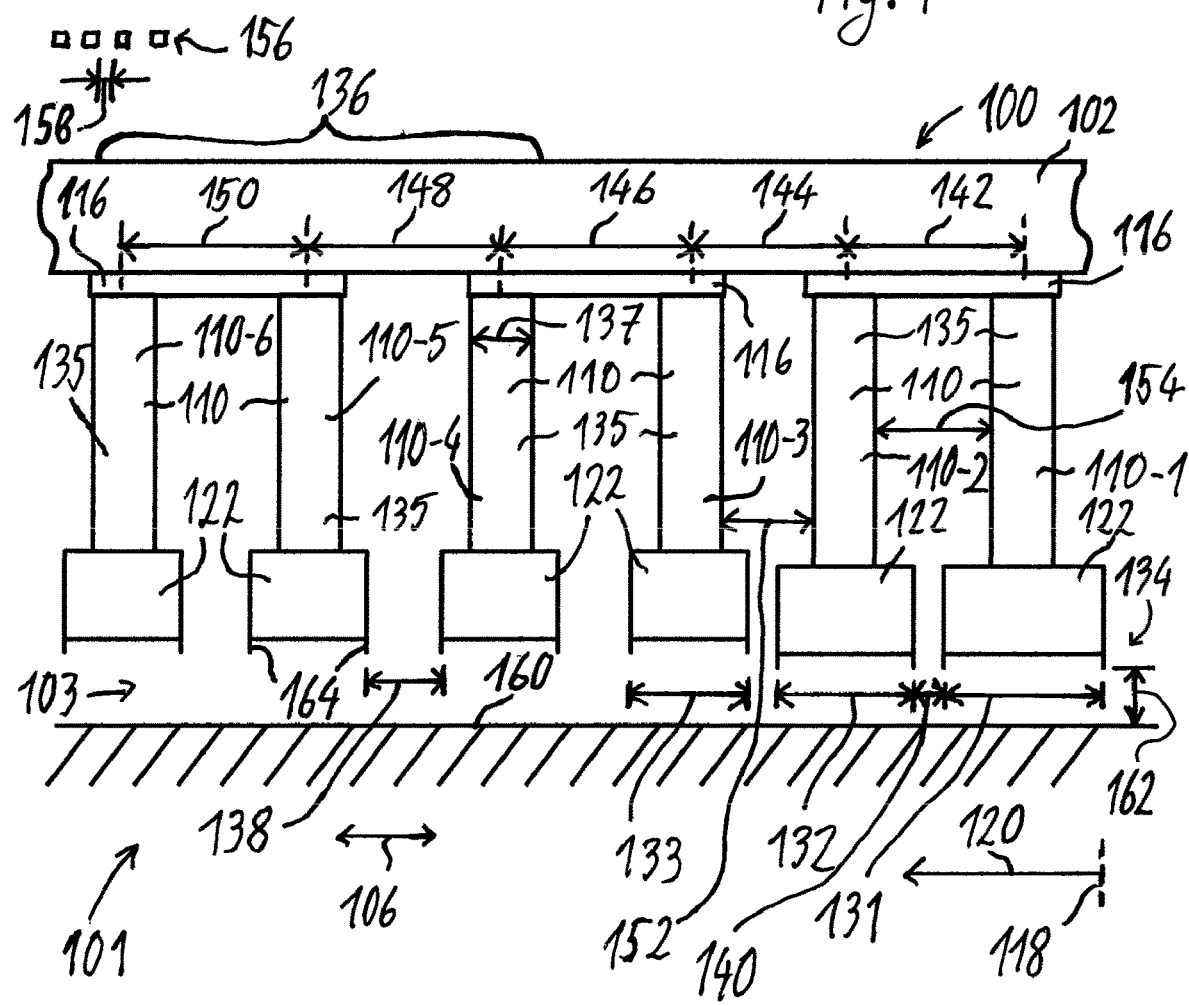
FIG. 2 schematically shows a plug-flow fermentation device according to embodiments of the herein disclosed subject matter.

FIG. 2 schematically shows a plug-flow fermentation device 103 according to embodiments of the herein disclosed subject matter. In particular, FIG. 2 schematically shows some aspects of a stirring device 100 according to embodiments of the herein disclosed subject matter.

It is noted that FIG. 2 does not provide angular position information of the stirring elements 110. Rather, the stirring elements 110 are shown in the same angular position in order to facilitate illustrating of other aspects herein disclosed subject matter. Unless noted to the contrary, positions of stirring elements and distances between stirring elements are hence axial positions/axial distances, e.g. distances between the stirring elements in the axial direction.

According to an embodiment, the stirring device 100 is located in a plug-flow fermenter 101 (also referred to as "fermenter" for short) of a plug-flow fermentation device 103. FIG. 2 shows in particular a first stirring element 110-1, a second stirring element 110-2, and a third stirring element 110-3. In accordance with an embodiment, the first stirring element 110-1 is a boundary stirring element defining the axial extent of the stirring volume covered by the stirring device the axial extent of the stirring volume covered by the stirring device 100 is indicated by a volume boundary 118 in FIG. 2 wherein an arrow 120 indicates a direction in which the stirring volume extends from the volume boundary 118.

According to a further embodiment, the second stirring element 110-2 is a nearest neighbor of the first stirring element 110-1 in the axial direction 106. In accordance with an embodiment, the third stirring element 110-3 is a next nearest neighbor of the first stirring element 110-1 in the axial direction 106 and is a nearest neighbor of the second stirring element 110-2 in the axial direction 106. Each of the stirring elements 110 comprises a head 122. According to an embodiment, the head 122 defines the maximum width of each stirring element 110 in the axial direction 106. In particular, the first stirring element 110-1 has a first maximum width 131, the second stirring element 110-2 has a second maximum width 132 and the third stirring element 110-3 has a third maximum width 133. According to an embodiment, each stirring element 110 comprises a rod portion 135 which extends between the mounting structure, e.g. the common mounting structure 116, associated with the stirring element 110 and its head 122. According to an embodiment, the rod portion 135 has a width 137 in the axial direction 106 which is smaller than the width of the head 122 in the axial direction 106. According to an embodiment, the rod portion 135 is identical or at least similar for all stirring elements 110 of the stirring device 100. However, it should be understood that in some embodiments the rod portion 135 may be adapted to the rated load of the particular stirring element.

According to an embodiment, in the axial direction 106 the maximum width 132 of the second stirring element 110-2 is smaller than the maximum width 131 of the first stirring element 110-1 and is larger than the maximum width 133 of the third stirring element 110-3. This increasing maximum width of the stirring elements 110 towards the boundary stirring element 110-1 results in an improved reduction of sediment in the region of the boundary stirring element 110-1. According to an embodiment, the boundary stirring element (the first stirring element 110-1) is located at a discharge region 134 of the plug-flow fermenter 101.

According to an embodiment, the stirring device comprises a further (axial) region 136, e.g. different from the discharge region 134 (or different from the region in which the first to third stirring elements 110-1, 110-2, 110-3 are located). According to an embodiment, in the further region of the stirring device two axially neighboring stirring elements 110-4, 110-5 define in the axial direction 106 a first minimum distance 138 (first axial minimum distance) therebetween.

According to an embodiment, the axial minimum distance between two axially neighboring stirring elements 110 is defined by the axial minimum distance of the sweeping ranges of the stirring elements 110. As usual, the sweeping range of a stirring element is defined by the space that is required by the stirring element 110 for its rotation about the axis of rotation 104 of the stirring device 100 (i.e. upon rotation of the shaft 102). According to an embodiment, the (axial) minimum distance (e.g. the first minimum distance 138) between two axially neighboring stirring elements 110 is defined by the extent of their heads 122 in the axial direction 106, as shown in FIG. 2. The first stirring element 110-1 and the second stirring element 110-2 define in the axial direction 106 a second (axial) minimum distance 140 therebetween. According to an embodiment, the first (axial) minimum distance 138 is larger than the second (axial) minimum distance 140. A smaller axial minimum distance (distance in axial direction) between stirring elements 110 in the discharge region also promotes reduction of sediments in the discharge region 134.

According to an embodiment, the positions of the first stirring element 110-1 and the second stirring element 110-2 are spaced by a first distance 142 in the axial direction 106. According to a further embodiment, the positions of the second stirring element 110-2 and the third stirring element 110-3 are spaced by a second distance 144 in the axial direction 106. According to a further embodiment, the positions of the third stirring element 110-3 and the fourth stirring element 110-4 are spaced by a third distance 146 in the axial direction 106. According to a further embodiment, the positions of the fourth stirring element 110-4 and the fifth stirring element 110-5 are spaced by a fourth distance 148 in the axial direction 106. According to a further embodiment, the positions of the fifth stirring element 110-5 and a sixth stirring element 110-6 are spaced by a fifth distance 150 in the axial direction 106.

According to an embodiment, in the axial direction 106 towards the boundary stirring element 110-1 the distance 150, 148, 146, 144, 142 between positions of neighboring stirring elements 110 is reduced compared to a distance between positions of neighboring stirring elements in a middle region (not shown in FIG. 2) of the stirring device 100. According to an embodiment, the middle region of the stirring device 100 is a region in (or close to) an axial center (center in axial direction) of the stirring device 100. According to an embodiment, the middle region of the stirring device 100 is spaced by at least five stirring elements, e.g. at least eight stirring elements from the boundary stirring elements of the stirring device 100. According to an embodiment, the further region referred to herein is the middle region of the stirring device 100.

According to an embodiment, in the axial direction 106 towards the boundary stirring element 110-1 the distance 150, 148, 146, 144 between the positions of the stirring elements 110 is monotonically reduced up to the second stirring element 110-2. According to an embodiment, the distance 142 between the positions of the second stirring element 110-2 and the first stirring element 110-1 is larger than the distance 144 between the positions of the third stirring element 110-3 and the second stirring element 110-2. The monotonical reduction of the distance between the positions 110 of the stirring of elements 110 up to the second stirring element 110-2 may reduce sediments in the discharge region 134 of the fermenter 101. According to an embodiment, the distance between the positions of the stirring elements is monotonically reduced at least among the last five stirring elements 110-6 to 110-2 adjacent to the boundary stirring element 110-1 or, in another embodiment, at least among the last four (or the last three) stirring elements adjacent to the boundary stirring element 110-1.

If the rod portions 135 of the stirring elements 110 are identical, a distance in axial direction between positions of neighboring stirring elements 110 (i.e. a distance between axial positions of neighboring stirring elements 110) corresponds to a respective distance between the rod portions of the neighboring stirring elements 110. However, according to an embodiment generally a first distance 152 between the rod portion 135 of the third stirring element 110-3 and the rod portion 135 of the second stirring element 110-2 is different from a second distance 154 between the rod portion 135 of the second stirring element 110-2 and the rod portion 135 of the first stirring element 110-1. According to an embodiment, the first distance 152 between the rod portion 135 of the third stirring element 110-3 and the rod portion 135 of the second stirring element 110-2 is smaller than the second distance 154 between the rod portion 135 of the second stirring element 110-2 and the rod portion 135 of the first stirring element 110-1.

According to an embodiment, in the axial direction 106 the minimum distance 140 between the first stirring element 110-1 and the second stirring element 110-2 is less than R times a maximum size of particulate matter for which the fermenter 101 and the stirring device 100 are designed (e.g. are rated). According to an embodiment, the minimum distance 140 is less than three times the maximum size of particulate matter. According to an embodiment, the maximum size of particulate matter is the maximum allowable size for the particulate matter in at least two dimensions. According to an embodiment this maximum size is guaranteed size by a sieve (schematically illustrated at 156 in FIG.

2) through which the fermentation material is introduced into the fermenter 101. According to an embodiment, a mesh size 158 of the sieve 156 defines (corresponds to) the maximum size of particulate matter. It should be understood that the sieve 156 is usually located in an input path through which the fermentation material is introduced into the plug-flow fermenter 101.

According to an embodiment, the fermenter 101 comprises a fermenter wall 160 which defines a bottom of a cavity for receiving the fermentation material. According to an embodiment, a minimum distance 162 between the first stirring element 110-1 and the fermenter wall 160 is larger than S times the maximum size 158, wherein S is in an interval between $1 \leq S \leq 5$. For example, in an embodiment the minimum distance 162 is three times the maximum size 158. According to an embodiment, the stirring elements 110 comprise protrusions 164 (indicated for the fifth stirring element 110-5 in FIG. 2) which define the radial extent of the stirring element 110. Such protrusions 164 may be suitable for breaking up sediments with comparably low forces. Generally, the stirring elements 110 and in particular the heads 122 may be configured e.g. as described in European patent applications EP 2837420 A1 and EP 2 561 925 A1 filed by the same applicant.

Generally, reducing sediments helps to condition the fermentation material within the plug-flow fermenter 101 into a pumpable and/or suckable state. This is in particular helpful at the discharge region. If the fermentation material within the plug-flow fermenter is brought into a pumpable and/or suckable state at the discharge region, the discharge of the fermentation material and in particular the discharge of the particulate matter is promoted. Hence, the operation of the fermenter may be more reliable.

Figure 3:
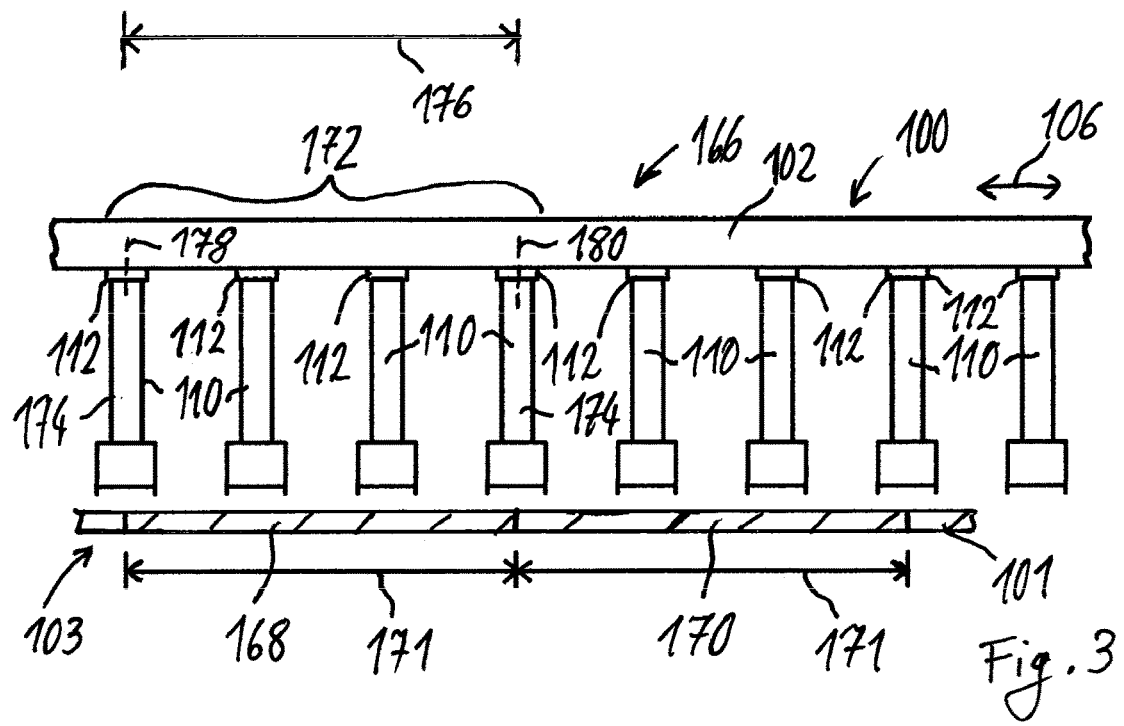
FIG. 3 shows a further part of the fermentation device of FIG. 2.

FIG. 3 shows a further part of the fermentation device 103 of FIG. 2. In particular, FIG. 3 shows a middle region 166 of the fermenter 101. Similar to FIG. 2, FIG. 3 does not provide any information about the angular position of the stirring elements 110. Rather, the stirring elements in FIG. 3 are only shown to illustrate the axial positions of the stirring elements 110 (i.e. the positions of the stirring elements 110 in the axial direction 106). Positions and distances among stirring elements described with regard to FIG. 3 are hence axial positions and axial distances.

According to an embodiment, except for at least one end region of the fermenter 101, e.g. the end region shown in FIG. 2 which comprises the boundary stirring element 110-1, e.g. in the middle region 166, the stirring device 100 comprises an individual mounting structure 112 for each stirring element 110.

According to an embodiment, the plug-flow fermenter 101 comprises a plurality of fermenter parts positioned subsequently in the axial direction 106. For example, according to an embodiment, the fermenter parts are bottom elements as described in European Patent Application EP 2 562 241 A1. In accordance with an embodiment, the plurality of fermenter parts comprise a first fermenter part 168 and a second fermenter part 170. The first fermenter part 168 and the second fermenter part 170 both have a first axial extent 171 (i.e. the first and second fermenter parts 168, 170 have the same first axial extent 171).

According to an embodiment, the plurality of stirring elements 110 comprise a sequence of stirring elements indicated at 172 in FIG. 3. In the axial direction 106 the sequence 172 of stirring elements is defined by two outermost stirring elements 174. The sequence 172 of stirring elements has a second axial extent 176 between the axial positions 178, 180 of the outermost stirring elements 174.

According to an embodiment, the first axial extent 171 and the second axial extent 176 differs by less than 5% of the first axial extent 171. For example, according to an embodiment, the first axial extent 171 and the second axial extent 176 are equal, as shown in FIG. 3. The adjustment of the first axial extent of the first fermenter part 168 and the second axial extent 176 of the sequence 172 of stirring elements has the advantage that the first fermenter part may be omitted together with the sequence 172 of stirring elements except for one of the outermost stirring elements 174 of the sequence 172. In this way, the fermentation device 101 may be configured in different sizes in axial direction without difficult calculations of the positions of the remaining stirring elements.

In a similar way, the second fermenter part 170 and the associated sequence of stirring elements (which are in the respective axial position of the second fermenter part 170) may be adjusted. In this case, the size of the fermentation device 101 may be changed by omitting one or both of the first fermenter part 168 and the second fermenter part 170 with the respective stirring elements.

According to an embodiment, the axial extent of the fermenter parts (e.g. the first axial extent of the first fermenter part 168) is smaller or equal than a size of a door opening of a standard ISO container. This has the advantage that the fermenter parts may be shipped in standard ISO containers.

Figure 4:
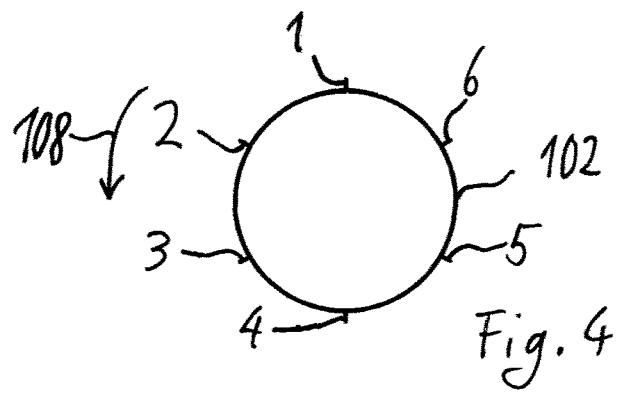
FIG. 4 shows a front view of a shaft of a stirring device according to embodiments of the herein disclosed subject matter.

FIG. 4 shows a front view of a shaft 102 of a stirring device according to embodiments of the herein disclosed subject matter. According to an embodiment, the plurality of stirring elements are arranged in at least two subsets on the shaft, wherein the stirring elements of each subset are positioned within an angular range of ±15 degrees. According to an embodiment, the angular range is smaller, e.g. ±10 degrees, ±5 degrees or ±1 degree. According to an embodiment, the stirring elements of each subset have the same angular position, at least within positioning tolerances. According to an embodiment, the stirring elements 110 are arranged in six subsets, the angular positions of which are indicated with the numbers 1 to 6 in FIG. 4. According to an embodiment, the subsets 1 to 6 are equally spaced in circumferential direction 108. In the example shown in FIG. 4, (with respect to subset 1) subset 1 corresponds to an angle of 0 degrees, subset 2 corresponds to an angle of 60 degrees, subset 3 corresponds to an angle of 120 degrees, subset 4 corresponds to an angle of 180 degrees, subset 5 corresponds to an angle of 240 degrees, and subset 6 corresponds to an angle of 300 degrees.

Figure 5:
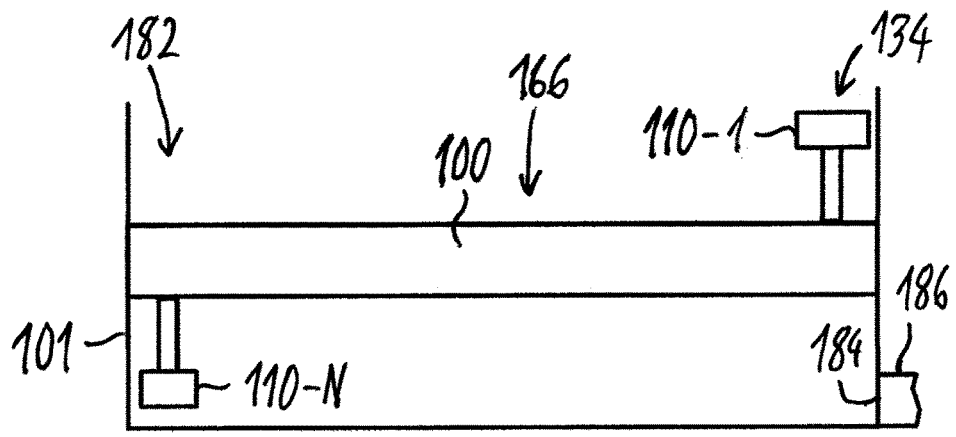
FIG. 5 shows a table indicating an example of an angular position of part of the plurality of stirring elements according to embodiments of the herein disclosed subject matter.

FIG. 5 shows a plug flow fermenter 101 according to embodiments of the herein disclosed subject matter.

According to an embodiment, the plug-flow fermenter 101 comprises a stirring device 100 according to embodiments of the herein disclosed subject matter. In FIG. 5 only the outermost stirring elements 110-1 and 110-N (also referred to as boundary stirring elements) are shown.

The plug-flow fermenter 101 comprises an input region 182 of the fermenter, where fresh fermentation material is introduced in the fermenter.

The angle between individual subsets is also referred to as partitioning angle of the stirring elements. According to an embodiment a minimum angular distance between two axially neighboring stirring elements is an integer multiple of the partitioning angle. For example, according to an embodiment the minimum angular distance between two neighboring stirring elements is double the partitioning angle.

According to an embodiment, in the end regions 134, 182 of the stirring device (i.e. in the vicinity of the boundary stirring elements 110-1 and 110-N, if the stirring device comprises a number of N stirring elements) the angular distance between neighboring stirring elements is larger than a minimum angular distance between neighboring stirring elements which is defined by the plurality of stirring elements of the stirring device. For example, in the end regions of the stirring device (i.e. in the vicinity of the boundary stirring elements 1 and N) the angular distance between neighboring stirring elements is larger than in regions that are spaced by a certain number of stirring elements from the boundary stirring elements.

According to an embodiment the number of stirring elements with larger angular distance between neighboring stirring elements, which define the end regions (input region 182 and discharge region 134) is between three and twelve. According to an embodiment the region between these end regions 134, 182 is referred to as middle region 166 of the stirring device.

According to a further embodiment, the angular positions of the sequence 172 of stirring elements (see FIG. 3) are configured such that omitting the sequence 172 of stirring elements except for one of the outermost stirring elements 174 of the sequence 172 does not increase the difference of the number of stirring elements among the subsets by more than one. For example, according to an embodiment the angular positions of the sequence 172 of stirring elements are configured such that omitting the sequence 172 of stirring elements except for one of the outermost stirring elements 174 of the sequence 172 does not remove more than one stirring element from each subset of stirring elements.

In accordance with further embodiments of the herein disclosed subject matter, the following considerations are taken into account in actual implementations or when combining embodiments of the herein disclosed subject matter:

Depending on the axial position in the fermenter (input region, middle region, discharge region) and the respective load on the stirring elements, different stirring elements may be mounted to the shaft in the different regions. For example, in the input region and in the discharge region stirring elements which are rated for a higher load may be used compared to stirring elements in the middle region of the stirring device. Further, in the input region the fermentation material has a higher dry matter content which results in a higher agitation resistance. Depending on the type of input (e.g. whether or not the fresh fermentation material is subjected to a mixing device before introducing the fresh fermentation material into the fermenter) the agitation resistance may change upon input of the fresh fermentation material into the plug-flow fermenter. If a direct input (introduction of fresh fermentation material into the plug-flow fermenter without subjecting the same to a mixing device) is used, the fermentation material requires more of homogenization in the input region. Usually in the discharge region the dry matter content and the agitation resistance associated therewith is lower. However, if sediments at the bottom of the plug-flow fermenter are not avoided in the discharge region higher forces may occur. Further, an edge at a discharge outlet 184 in the plug-flow fermenter (leading to an outlet duct 186) may increase the likelihood of particulate matter being jammed between the stirring device and the edge which requires higher force to be transferred by the stirring device. Further, in the discharge region stirring elements with a larger extent in axial direction may result in higher forces. In an embodiment, due to the influences described above the agitation resistance of the boundary stirring element in the input region as well as in the discharge region are similar (e.g. approximately identical).

An equal spacing of stirring elements (e.g. measured in the position of the stirring elements or in the axial minimum distance of the rod portions of the stirring elements) may be desirable in order to avoid sediment piling up in a region of larger spacing between stirring elements. Embodiments of the herein disclosed subject matter may provide the advantage of homogenizing the fermentation material in the discharge region of the fermenter and may reduce or prevent obstructing of an outlet of the fermenter through which the fermentation material in the discharge region within the fermenter is discharged from the fermenter. According to embodiments of the herein disclosed subject matter, by homogenizing the fermentation material in the discharge region the transport principle changes from "plug-flow" to "pumpable" or "suckable" in the discharge region 134 of the fermenter. Hence, in accordance with an embodiment, fermentation material in the discharge region can be discharged from the discharge region (i.e. the discharge is at least supported) by a discharge pump in a discharge path through which fermentation material is transported from the fermenter to e.g. a dewatering device.

If a heating element is positioned between two neighboring stirring elements, the distance between these neighboring stirring elements may be increased, e.g. by 5% to 20%, e.g. by 15%. According to an embodiment, if a distance from one stirring element to a first nearest neighbor stirring element (in plug-flow direction) is increased (e.g. due to space required for a heating element), a distance from the one stirring element to a second nearest neighbor stirring element (on the opposite side, opposite the plug-flow direction) is decreased to at least partially compensate for the increase. According to an embodiment such compensation may be performed on both sides of the increased distance, e.g. by a half compensation on each side. In this regard and generally herein the term "approximately the same" or "the same" means, in an embodiment, the "same within a tolerance window of ±15%". In other embodiments, the tolerance window may be ±5% or ±2%. According to an embodiment, "the same within a tolerance window of ±x %" means that each value of a number of individual values differs from an arithmetic mean value, which is calculated from the individual values, by ±x % or less.

Generally, it is noted that the different types of fermentation material without the agitation by the stirring device would result in a de-mixing of the fermentation material. In particular, heavy fermentation material would sink down and form a layer of sediment. Light fermentation material would move to and remain at the surface of the fermentation material in the fermenter. Fermentation material of the fiber type would move up due to its contact with gas bubbles and would mat (felt) into a floating layer. The floating layer would disturb the operation of the fermenter and the discharge of gas out of the fermentation material. By the agitation of the fermentation material by the stirring device the discharge of gas out of the fermentation material is supported. The stirring device has to cope with sediments, heavy fermentation material and extraneous material. The sediment has to be transported through the fermenter although the plug-flow is not large enough to accomplish this. Due to the agitation of the fermentation material the input of heat into the fermentation material (and/or the distribution of heat in the fermentation material) in the vicinity of heating elements is improved. Heating elements include for example heating elements at the bottom of the fermenter and in the vicinity of heating elements that extend into the fermentation material. Due to the input of a cold fermentation material the input region requires the largest heating power density. By reducing the distance between the stirring elements and the fermenter wall the thickness of sediment is reduced and the heat transfer is improved (usually the sediment has a comparatively low thermal conductivity, compared to the average fermentation material). Also, by reducing the distance between the stirring elements and the fermenter wall material currents are increased.

It should be noted that any entity disclosed herein (e.g. components, elements and devices) are not limited to a dedicated entity as described in some embodiments. Rather, the herein disclosed subject matter may be implemented in various ways and with various granularity on device level while still providing the specified functionality. Further, it should be noted that according to embodiments a separate entity may be provided for each of the functions disclosed herein. According to other embodiments, an entity is configured for providing two or more functions as disclosed herein. According to still other embodiments, two or more entities are configured for providing together a function as disclosed herein.

Further, although some embodiments refer to specific entities, e.g. a common mounting structure, it should be understood that each of these references is considered to implicitly disclose in addition a respective reference to the corresponding general term (e.g. a "mounting structure"). Also, other terms which relate to specific techniques are considered to implicitly disclose the respective general term with the specified functionality.

Further, it should be noted that while the exemplary elements and devices in the drawings comprise a particular combination of several embodiments of the herein disclosed subject matter, any other combination of embodiment is also possible and is considered to be disclosed with this application and hence the scope of the herein disclosed subject matter extends to all alternative combinations of two or more of the individual features mentioned or evident from the text. All of these different combinations constitute various alternative examples of the invention.

It should be noted that the term "comprising" does not exclude other elements or steps and the article "a" or "an" does not exclude a plurality. Also, elements described in association with different embodiments may be combined.

In order to recapitulate some of the above described embodiments of the present invention one can state:

A stirring device 100 of a plug-flow fermentation device 103 comprises a shaft 102 rotatable about an axis of rotation 104 which defines an axial direction 106. The stirring device 100 further comprises a boundary stirring element 110-1 that defines the axial extent of a stirring volume covered by the stirring device 100. A nearest neighbor 110-2 of the boundary stirring element 110-1 in the axial direction 106 has an axial maximum width 132 which is smaller than an axial maximum width 131 of the boundary stirring element 110-1 and which is larger than an axial maximum width 133 of a next-nearest neighbor 110-3 of the boundary stirring element 110-1.

The invention claimed is:

1. A plug-flow fermentation device for receiving a fermentation material and for fermentation of the fermentation material, the plug-flow fermentation device being a biogas plant comprising:
   a plug-flow fermenter; and
   a stirring device of the plug-flow fermenter,
   the stirring device having
      a shaft rotatable about an axis of rotation, the axis of rotation being parallel to an axial direction;
      a plurality of stirring elements including a first stirring element, a second stirring element and a third stirring element;
      wherein the first stirring element is a boundary stirring element located in one of an input region and a discharge region and defining an axial extent of a stirring volume covered by the stirring device;
      the second stirring element is a nearest neighbor of the first stirring element in the axial direction;
      the third stirring element is a next-nearest neighbor of the first stirring element in the axial direction; and
      in the axial direction the second stirring element has a maximum width which is smaller than a maximum width of the first stirring element and which is larger than a maximum width of the third stirring element.

2. The plug-flow fermentation device according to claim 1, further comprising:
   a common mounting structure being associated with two axially neighboring stirring elements of the plurality of stirring elements;
   wherein the two axially neighboring stirring elements are both mounted to the shaft via the common mounting structure.

3. The plug-flow fermentation device according to claim 1,
   wherein the rotation of the shaft about the axis of rotation defines a circumferential direction; and
   wherein in the circumferential direction the third stirring element is located in an angular range between the first stirring element and the second stirring element.

4. The plug-flow fermentation device according to claim 1,
   wherein the second stirring element is located opposite the first stirring element, in an angular range between 140 degrees and 220 degrees with respect to the first stirring element.

5. The plug-flow fermentation device according to claim 1,
   wherein the plurality of stirring elements are arranged in at least two on the shaft, the at least two subsets including a first subset and a second subset, wherein the stirring elements of each subset are positioned within an angular range of ±15 degrees; and
   wherein the first stirring element belongs to the first subset, and wherein in the first subset there are fewer stirring elements than in the second subset.

6. The plug-flow fermentation device according to claim 1,
   further comprising two further, axially neighboring stirring elements defining in the axial direction a first minimum distance therebetween;
   the first stirring element and the second stirring element defining in the axial direction a second minimum distance therebetween; and
   wherein the first minimum distance is larger than the second minimum distance.

7. The plug-flow fermentation device according to claim 1,
   wherein in the axial direction towards the boundary stirring element a distance between positions of neighboring stirring elements is reduced compared to a distance between positions of neighboring stirring elements in a middle region of the stirring device.

8. The plug-flow fermentation device according to claim 1,
wherein each of the stirring elements comprises a rod portion having a first width in the axial direction and a head portion which has a second width in the axial direction; and
wherein in the axial direction towards the boundary stirring element the second width of the stirring elements increases.

9. The plug-flow fermentation device according to claim 8, further comprising:
a first distance between the rod portion of the third stirring element and the rod portion of the second stirring element; and
a second distance between the rod portion of the second stirring element and the rod portion of the first stirring element;
wherein the first distance is different from the second distance.

10. The plug-flow fermentation device according to claim 1,
the stirring device being designed for fermentation material the particulate matter of which has in at least two dimensions a size which is smaller than or equal to a predetermined maximum size; and
wherein in the axial direction a minimum distance between the first stirring element and the second stirring element is less than R times the maximum size, wherein R is a number in an interval $1 \leq R \leq 5$.

11. The plug-flow fermentation device according to claim 1,
wherein the stirring device is designed to be located in a plug-flow fermenter of the plug-flow fermentation device such that the first stirring element is located in a discharge region of the plug-flow fermenter.

12. The plug-flow fermentation device according to claim 1, further comprising:
a fermenter wall defining a bottom of the plug-flow fermenter for receiving the fermentation material;
the plug-flow fermentation device being configured for introduction of fermentation material the particulate matter of which has in at least two dimensions a size which is smaller than or equal to a predetermined maximum size; and
wherein a minimum distance between the first stirring element and the fermenter wall is larger than S times the maximum size, wherein S is a number in an interval $1 \leq S \leq 5$.

13. The plug-flow fermentation device according to claim 1,
the plug-flow fermenter comprising a plurality of fermenter parts positioned subsequently in the axial direction, the plurality of fermenter parts comprising a first fermenter part having a first axial extent in the axial direction;
the plurality of stirring elements comprising a sequence of stirring elements, the sequence of stirring elements being defined in the axial direction by two outermost stirring elements of the sequence, the sequence of stirring elements having a second axial extent between the axial positions of the outermost stirring elements;
wherein the second axial extent differs from the first axial extent by less than 5% of the first axial extent.

14. A method of operating a plug-flow fermentation device in a biogas plant, the method comprising:
providing fermentation material to a plug-flow fermenter; and
stirring with a stirring device in the plug-flow fermenter, the fermentation material which contains heavy particulate matter so as to homogenize the fermentation material at an end region of the plug-flow fermenter;
wherein homogenizing the fermentation material includes dispersing the heavy particulate matter within the fermentation material, the plug-flow fermentation device comprising:
a plug-flow fermenter; and
a stirring device located in the plug-flow fermenter,
the stirring device having
a shaft rotatable about an axis of rotation, the axis of rotation being parallel to an axial direction;
a plurality of stirring elements including a first stirring element, a second stirring element and a third stirring element;
wherein the first stirring element is a boundary stirring element located in one of an input region and a discharge region defining an axial extent of a stirring volume covered by the stirring device;
the second stirring element is a nearest neighbor of the first stirring element in the axial direction;
the third stirring element is a next-nearest neighbor of the first stirring element in the axial direction; and
in the axial direction the second stirring element has a maximum width which is smaller than a maximum width of the first stirring element and which is larger than a maximum width of the third stirring element.

* * * * *